United States Patent [19]

Buckley et al.

[11] Patent Number: 4,985,298

[45] Date of Patent: Jan. 15, 1991

[54] ABSORBENT NONWOVEN WEBS

[75] Inventors: Lee A. Buckley, White Bear Lake; Thomas I. Insley, Lake Elmo, both of Minn.

[73] Assignee: Minnesota Mining and Manufacturing Company, St. Paul, Minn.

[21] Appl. No.: 418,698

[22] Filed: Oct. 2, 1989

Related U.S. Application Data

[63] Continuation of Ser. No. 235,691, Aug. 18, 1988, abandoned, which is a continuation of Ser. No. 687,828, Dec. 3, 1984, abandoned.

[51] Int. Cl.$^5$ ............ A61F 13/20; A61F 13/36; B32B 27/04; B32B 27/26
[52] U.S. Cl. ................. 428/288; 128/113.1; 428/290; 604/372
[58] Field of Search ............ 428/288, 290; 604/372

[56] References Cited

U.S. PATENT DOCUMENTS

| | | | |
|---|---|---|---|
| 3,686,024 | 8/1972 | Nankee et al. | 428/296 |
| 3,903,889 | 9/1975 | Torr | 128/287 |
| 4,059,114 | 11/1977 | Richards | 128/287 |
| 4,235,237 | 11/1980 | Mesek et al. | 128/284 |
| 4,429,001 | 1/1984 | Kolpin | 428/303 |

Primary Examiner—James C. Cannon
Attorney, Agent, or Firm—Donald M. Sell; Walter N. Kirn; Carole Truesdale

[57] ABSTRACT

Highly absorbent nonwoven webs formed from readily available nonwoven materials and having a polyelectrolyte super-absorbent polymeric sorbent coating the individual fibers of the nonwoven web are disclosed. The polymeric sorbent coating absorbs liquid while minimizing occlusion of the interstices of the web.

9 Claims, No Drawings

4,985,298

ABSORBENT NONWOVEN WEBS

This is a continuation of application Ser. No. 07/235,691, filed Aug. 18, 1988, now abandoned, which is a continuation of application Ser. No. 687,828, filed Dec. 31, 1984, now abandoned.

BACKGROUND OF THE INVENTION

The present invention relates to a highly absorbent nonwoven web formed from readily available nonwoven materials and a polyelectrolyte super-absorbent polymer.

Absorbent sheet materials have been obtained through the incorporation of super-absorbent polymers onto various carrier substrates. In most of these materials, the carrier substrate is used to provide the mechanical support for the absorbent components which have little or no mechanical stability per se. Approaches to providing sorbent/carrier composites have varied, often involving the combination of film or particulate forms of super-absorbent polymer in sandwich or laminate types of construction. (See U.S. Pat. Nos. 4,008,353 and 4,190,562).

In some of these constructions, highly localized concentrations of super-absorbent polymers are layered between two substrates with at least one side of the final structure being water permeable. Other constructions are known in which the sorbent is coated onto the top or bottom or both sides of a nonwoven web. While these composites include substantial amounts of super-absorbent materials, they do, nonetheless, have inherent drawbacks which become evident in particular applications. Thus, where the need for rapid uptake of liquid is an essential performance criterion, especially where the super-absorbent polymers are the primary absorbent constituent, the highly localized (planar) concentration of the super-absorbent polymers causes these composites to suffer from the effects of the gel blocking phenomenon of super-absorbent polymers. Super-absorbent polymers, by their nature, swell but do not dissolve upon contact with water. It is this mechanism that allows these materials to imbibe and retain large amounts of liquids. While super-absorbent polymers are excellent for the containment of water (swelling occurs through osmotic effects), liquid transport through the gel occurs primarily by diffusion and is necessarily limited in rate. If several layers of planar-dispersed super-absorbent polymer are used, then the gel layer produced upon wetting of the surface layer closest to the liquid source, will act essentially as a liquid barrier. These effects are widely recognized and in some instances can provide desirable results. U.S. Pat. No. 3,888,256 discloses a diaper construction in which a particulate swelling substance is arranged in one of the layers closest to the baby's skin. The particles are distributed such that: their spacing allows for an initial passage of liquid (urine), but as the particles swell upon wetting, they close off the open portion of the web and ultimately provide a barrier to back-flow of liquid.

When a barrier effect is not desirable, which would be the case where the super-absorbent polymer is the primary absorbent component, then alternate dispersion schemes must be utilized. Methods for producing near homogeneous dispersions of super-absorbent polymers in open network systems have involved both liquid and air carrier methods for incorporation of the water swellable but water insoluble super-absorbent polymers into the open network. In the liquid carrier method, swollen super-absorbent polymer particles in an aqueous suspension are deposited onto the substrate surface and the liquid carrier evaporated to produce an anchored super-absorbent polymer composite. (U.S. Pat. Nos. 4,235,235 and 3,686,024).

Swollen gel particles at even moderate concentrations in an aqueous system are very viscous suspensions and are inherently difficult to handle from a processing standpoint. If lower suspension concentrations are used to reduce the viscosity effects, then a need to remove proportionately larger amounts of liquid carrier becomes necessary in an evaporation step. Alternate methods of controlled deposition utilize air as the super-absorbent polymer carrier (U.S. Pat. No. 4,429,001). While this method overcomes many of the process related drawbacks of wet deposition, these composites retain the particulate super-absorbent polymer in the web through mechanical entrapment thereby presenting an opportunity for some loss (by dusting out) of the super-absorbent polymer component.

SUMMARY OF THE INVENTION

The present invention relates to an improved open network sorbent web, in which a thin filmy coating of super-absorbent polymer is formed on the individual fibers of a nonwoven carrier substrate. The composite nonwoven webs of the present invention are particularly useful for liquid absorption and retention applications, and are advantageously utilized in diapers, sanitary napkins, incontinent devices and as wound dressings.

DETAILED DESCRIPTION OF THE INVENTION

The highly absorbent nonwoven webs of the present invention are produced by a method which involves curing (crosslinking) a super-absorbent prepolymer impregnant in situ such as through drying of a nonwoven web impregnated with an aqueous solution of the prepolymer. The prepolymer can consist of a saponified carboxylic polyelectrolyte such as: acrylic acid—acrylate copolymers; acrylic acid—acrylamide copolymers; acrylic acid—olefin copolymers polyacrylic acid; acrylic acid—vinyl aromatic copolymers; acrylic acid—styrene sulfonic acid copolymers; acrylic acid—vinyl ether copolymers; acrylic acid—vinyl acetate copolymers; acrylic acid—vinyl alcohol copolymers; copolymers of methacrylic acid with all the above comonomers; copolymers of maleic acid, fumaric acid and their esters with all the above comonomers; copolymers of maleic anhydride with all the above comonomers; or graft polymers containing gelatinized starch and saponified polyacrylonitrile or polymethacrylonitrile.

Examples of crosslinking agents useful in the invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin, and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Compounds containing two or more functional groups of the foregoing crosslinking agents would be expected to be likewise useful, as well as precursors which would form these functional groups under the conditions encountered in heating or drying the polyelectrolyte solutions.

Sulfonium zwitterions are known from U.S. Pat. No. 3,660,431; U.S. Pat. No. 3,749,737 and U.S. Pat. No. 3,749,738.

The resulting polymer-containing nonwoven product has particularly useful liquid absorbent and retention characteristics. The absorbent porous web thus comprises a nonwoven fibrous three dimensional network of staple fibers having a thin but continuous coating of a super-absorbent polymeric sorbent on the individual fibers, the fibrous network being unified by the polymeric coating essentially only at the crossing points of the fibers such that the polymeric coating upon sorption of liquid swells with minimum occlusion of the interstices of the web. The polymeric sorbent is not readily discernible within the interstices of the web, even upon microscopic examination.

This open network sorbent system can be comprised of from 60 to 99+ percent void volume. Void volume was determined by an Air Comparison Pycnometer (Beckman model 9030 using the Standard Operation Mode).

Preferred embodiments of this invention utilize as the carrier substrate a three-dimensional open network structure formed from a plurality of fibers in random point contact with one another. Nonwoven webs produced on a Rando Webber machine or a carding machine are suitable substrates. The nonwoven web is saturated with a sorbent prepolymer composition; the bulk of the sorbent prepolymer composition is removed and the prepolymer cured in situ by drying the web in an oven. The resulting composite comprises individual fibers sheathed in super-absorbent polymer and bonded together at their crossing points by the cured polyelectrolyte super-absorbent polymer. In this fashion, the carrier web retains its open network structure and provides not only structural support for the super-absorbent polymer but also provides the optimum sorbent surface area and super-absorbent polymer distribution throughout the web which minimizes gel blocking effects.

Tests useful in evaluating the sorbency of the webs of the present invention and their ability to retain the absorbed liquid under pressure include the following:

DEMAND SORBENCY TEST

A 1.75 inch (4.45 cm) diameter test sample of web is placed on a 25–50μ porous plate in a filter funnel. A pressure of 1.0 kPa is applied to the sample by a plunger which is freely movable in the barrel of the funnel. Test fluid at zero hydrostatic head is conducted from a reservoir through a siphon mechanism to the upper surface of the porous plate where the test sample sorbs the fluid. The amount of fluid withdrawn from the reservoir by the test sample is then measured to determine the amount of fluid sorbed by the test sample.

CENTRIFUCAL RETENTION TEST

A 1 g sample of web is placed in a centrifuge basket and the basket with sample is submerged in a test solution for up to three hours. The basket with sample is removed, drained for 2–3 minutes, and placed in a centrifuge tube. The tube is placed in a centrifuge and subjected to a centrifugal force of 180 G for 10 minutes. The sample is removed and the amount of test solution retained is measured.

In the Demand Sorbency Test and the Centrifugal Retention Test synthetic urine (S.U.) is used as the test liquid. The synthetic urine had the following formulation:

| | |
|---|---|
| 0.06% | calcium chloride |
| 0.10% | magnesium sulfate |
| 0.83% | sodium chloride |
| 1.94% | urea |
| 97.07% | deionized water |

The synthetic urine solution has a conductance of 15.7 mΩ.

The following examples will more fully illustrate the invention. It will be apparent that a variety of substrates can be utilized in carrying out the present invention.

EXAMPLES 1-6

A sorbent prepolymer composition was prepared in the following manner:

300.9 grams of saponified ethyl acrylate/methacrylic acid dispersion (approx. 12% solids) (Dow XD-8587.01, Dow Chemical Co.) were combined with an equivalent amount of deionized water and 4.2 grams of a non-ionic surfactant (Triton X-100, Rohm & Haas).

The mixture was stirred over low heat on a hot plate and 6.0 grams of cross-linking agent (CX-100, Polyvinyl Chemical Industries) was added.

A dry fluffy fibrous web was formed on a Rando Webber utilizing a 6 dpf×64 mm Chisso web with a basis weight of 190 g/m$^2$ (Chisso Corp., Japan). The web was unified by thermal setting of the fibers. The sorbent prepolymer composition was then applied to the substrate at three resulting levels: 48, 60 & 66 weight % sorbent (total weight of web plus sorbent). At each level four samples were impregnated using the method described below.

Round 1.75 inch (4.45cm) die cut samples of the dry fluffy sheet were saturated with the sorbent prepolymer composition. The majority of the sorbent prepolymer composition was then removed from the void spaces within the substrate by centrifuging. The samples were centrifuged for various lengths of time to obtain different amounts of sheathing of the fibers. The samples, were cured for 12 hours at 150° F. (65° C.) in an oven.

At each of these same three levels, i.e., 48, 60 and 66 weight percent, four additional samples were "coated" as described in U.S. Pat. No. 3,686,024.

Samples were then tested for liquid absorption using the Demand Sorbency Test and retention using the Centrifugal Retention Test. Absorption and retention values of the various levels of sorbent are shown in Tables I and II.

TABLE I

| Example | Method | Basis Wt g/m² | Wt % Sorbent | Absorption g S.U./g sorb | Absorption g S.U./g matl | Retention g S.U./g sorb | Retention g S.U./g matl |
|---|---|---|---|---|---|---|---|
| 1 | Impregnated | 188 | 48 | 49.8 | 23.8 | 16.1 | 7.2 |
| 2 | Impregnated | 194 | 60 | 48.6 | 22.5 | 20.9 | 9.1 |
| 3 | Impregnated | 180 | 66 | 35.2 | 22.7 | 16.8 | 10.5 |
| 4 | U.S. Pat. No. 3,686,024 | 188 | 48 | 16.9 | 7.9 | 14.9 | 6.4 |
| 5 | U.S. Pat. No. 3,686,024 | 194 | 60 | 13.8 | 8.1 | 12.5 | 6.9 |
| 6 | U.S. Pat. No. 3,686,024 | 180 | 66 | 13.8 | 9.0 | 12.6 | 7.9 |

TABLE II

| | Weight of Liquid Absorbed for Time Shown (1/m²) | | | | | |
|---|---|---|---|---|---|---|
| Example | 5 min | 10 min | 15 min | 20 min | 25 min | 30 min |
| 1 | 2.5 | 4.9 | 6.7 | 7.7 | 8.1 | — |
| 2 | 2.6 | 5.4 | 7.5 | 9.1 | 10.1 | 10.5 |
| 3 | 2.5 | 5.5 | 7.9 | 9.7 | 10.8 | 11.5 |
| 4 | 1.4 | 2.3 | 2.5 | 2.7 | 2.8 | — |
| 5 | 1.1 | 2.6 | 3.2 | 3.4 | 3.6 | 3.8 |
| 6 | 0.8 | 2.4 | 3.6 | 4.1 | 4.4 | 4.5 |

As the data from the two methods of sorbent application are compared (Tables I & II), the superior sorbent properties of the impregnated open network system of the present invention become obvious. The impregnated open network system utilizes the sorbent more effectively resulting in an absorption almost three times that of the "coated" method of U.S. Pat. No. 3,686,024 as well as superior retention. Upon inspection of the rate of absorption data, shown in Table II, it is seen that the open network web of the present invention absorbed the fluid nearly twice as fast as the "coated" material due to its enhanced fluid transport properties, i.e., freedom from gel blocking effects.

EXAMPLES 7-10

Round 1.75 inch (4.45cm) samples were die cut from a thermally set fibrous web comprised of 50% by weight 4 dpf×51 mm all polyester sheathed fibers and 50% by weight of polyester staple fibers, 15 dpf×31.5 mm, Type 431, semi-dull, crimped (Eastman Chemical Products Inc.) at a basis weight of 128 g/m². The all polyester sheathed fiber is believed to comprise a core of polyethylene terephthalate and a sheath of polyester resin comprising a random copolyester composite of 68% terephthalic acid units and 32% isophthalic acid units polymerized with ethylene glycol, and is available as Melty Fiber Type 4080 from Unitika, Ltd., Osaka, Japan.

The sorbent prepolymer composition of Examples 1-3 was prepared and the samples were processed and tested according to the procedure set forth in Example 1-3. The absorption and retention data are shown in Tables III and IV.

TABLE III

| Example | Basis weight g/m² | Wt. % sorb. | Absorption g S.U./g sorbent | Absorption g S.U./g material | Retention g S.U./g sorbent | Retention g S.U./g material |
|---|---|---|---|---|---|---|
| 7 | 128 | 35 | 69.1 | 24.7 | 26.0 | 8.7 |
| 8 | 128 | 50 | 40.6 | 20.4 | 19.2 | 9.1 |
| 9 | 128 | 53 | 41.0 | 21.9 | 22.8 | 11.7 |
| 10 | 128 | 66 | 23.1 | 15.11 | 16.8 | 10.6 |

TABLE IV

| | Weight of Liquid Absorbed for Time Shown (1/m²) | | | | |
|---|---|---|---|---|---|
| Example | 5 min | 10 min | 15 min | 20 min | 25 min |
| 7 | 0.21 | 0.45 | 0.63 | 0.78 | 0.91 |
| 8 | 0.35 | 0.72 | 0.99 | 1.20 | 1.38 |
| 9 | 0.30 | 0.67 | 1.00 | 1.30 | 1.56 |
| 10 | 0.40 | 1.01 | 1.50 | 1.89 | 2.19 |

Examination of Table III and IV shows that there is an optimum sheathing level of the fibrous substrate. For this substrate, approximately 60 weight percent of sorbent is optimum. Beyond this level, the efficiency of the sorbent decreased dramatically due to gel blocking.

EXAMPLES 11-14

Dry fluffy fibrous webs were formed according to the procedure set forth in Examples 1-3 from the following fiber constituents at the basis weights indicated.

Ex.11 - 15 dpf × 1½" (38.1 mm) polyester staple fibers with a vinyl chloride copolymer latex binder (Union Wadding); basis weight of 120 g/m².

Ex.12 - 6 dpf × 64 mm polyolefin thermal bonding bicomponent staple fibers, Type ES, (Chisso Corp., Japan); basis weight of 225 g/m².

Ex.13 - 43% by weight 5.5 dpf × 1¼" (31.75 mm) polyester staple fibers, T-435 Kodel, semi-dull, drawn, crimped (Eastman Chemical Prod., Inc.);
43% by weight 50 dpf × 2½" (63.5 mm) polyester staple fibers, crimped (3M Co.);
14% by weight 3 dpf × 1½" (38.1 mm), undrawn (thermal bonding) polyester staple fibers, semi-dull (Celanese Fibers Co.);
basis weight of 330 g/m².

Ex.14 - 9 dpf × 1¾" (44.45 mm) polypropylene staple fibers, Herculon, (Hercules, Inc.), needle tacked, basis weight of 240 g/m².

Round 1.75 inch (4.45 cm) die cut samples of each of the webs were impregnated with a sorbent prepolymer composition having the formulation set forth in Examples 1-3 and processed and testing according to the procedure set forth in Example 1-3. Liquid absorption and retention data are given in Table V and VI.

TABLE V

| Example | Fiber | Basis Wt g/m² | Wt % Sorbent | Absorption g. S.U./ g. sorb. | Absorption g. S.U./ g. matl. | Retention g. S.U./ g. sorb. | Retention g. S.U./ g. matl. |
| --- | --- | --- | --- | --- | --- | --- | --- |
| 11 | 15 dpf PET w/ binder | 120 | 74 | 31.4 | 22.2 | 18.6 | 13.4 |
| 12 | 6 dpf Chisso | 225 | 66 | 42.5 | 27.5 | 22.2 | 14.0 |
| 13 | 14% undrawn PET 43% 5.5 PET 43% 5 PET | 330 | 47 | 42.8 | 21.0 | 21.1 | 9.8 |
| 14 | 9 dpf PP needle tacked | 240 | 50 | 34.4 | 14.4 | 21.1 | 8.3 |

TABLE VI

| | Weight of Liquid Absorbed for Time Shown (1/m²) | | | | |
| --- | --- | --- | --- | --- | --- |
| Example | 20 min | 40 min | 60 min | 80 min | 100 min |
| 11 | 0.81 | 2.13 | 3.38 | 4.50 | 5.50 |
| 12 | 1.13 | 2.81 | 4.44 | 5.81 | 7.00 |
| 13 | 0.38 | 1.13 | 2.00 | 2.94 | 3.88 |
| 14 | 1.50 | 3.31 | 4.44 | 5.19 | 5.50 |

Examples 11–14 show that various fibrous substrates can effectively be utilized in the present invention.

EXAMPLE 15

A dry thin fibrous web consisting of 90% 1.5 dpf×1½" (38.1 mm) polyester staple fiber (Dupont) and 10% 4 dpf x 51mm all sheathed polyester, Melty Fiber Type 4080, was saturated with a sorbent prepolymer composition of 48% polymer (Dow XD-8587.01), 0.64% surfactant (Triton X-100), 50% DIW and 1.2% crosslinking agent (CX100), and the excess was squeezed off by running the web through a nip with 20 lbs. of pressure. The web was sent through a 290° F. (145° C.) oven (two passes). Absorption and retention data are shown in Tables VII and VIII.

TABLE VII

| Example | Basis Wt g/m² | Wt. % Sorbent | Absorption g S.U./g Sorbent | Absorption g S.U./g Material | Retention g S.U./g Sorbent | Retention g S.U./g Material |
| --- | --- | --- | --- | --- | --- | --- |
| 15 | 15.6 | 50 | 86.0 | 43.0 | 68.6 | 33.8 |

TABLE VIII

| | Weight of Liquid Absorbed for Time Shown (1/m²) | | | | |
| --- | --- | --- | --- | --- | --- |
| Example | 10 sec | 20 sec | 30 sec | 40 sec | 50 sec |
| 15 | 0.16 | 0.34 | 0.53 | 0.72 | 0.88 |

This example shows quite clearly that suitable absorbent webs can be produced utilizing pressure to remove excess prepolymer impregnant from the web before curing.

What is claimed is:

1. An absorbent porous web comprising a nonwoven fibrous three dimensional network of staple fibers, said fibers having a thin but continuous in situ cured coating of a super-absorbent polymeric sorbent thereon, said fibrous network being unified by said polymeric coating essentially only at the crossing points of said fibers such that said polymeric coating is not readily discernible within the interstices of the web even upon microscopic examination thereof, said polymeric coating, upon sorption of liquid, swelling with minimum occlusion of the interstices of the web.

2. An absorbent porous web according to claim 1 wherein said polymeric coating on said fibers comprises from 35 to 80 weight percent of the total web weight.

3. An absorbent porous web according to claim 1 wherein said coating on said fibers comprises about 60 weight percent of the total web weight.

4. An absorbent porous web according to claim 1 having an absorption capacity of at least 20 grams of synthetic urine per gram of polymeric sorbent.

5. An absorbent porous web according to claim 3 having an absorption capacity of at least 40 grams of synthetic urine per gram of polymeric sorbent.

6. A diaper containing the absorbent porous web of claim 1.

7. A feminine hygiene product containing the absorbent porous web of claim 1.

8. An incontinent device containing the absorbent porous web of claim 1.

9. A wound dressing containing the absorbent porous web of claim 1.

* * * * *